United States Patent
Habraken et al.

(10) Patent No.: US 6,408,051 B2
(45) Date of Patent: Jun. 18, 2002

(54) ELECTROMAGNETIC OBJECT DETECTOR PROVIDED WITH AN ADDITIONAL ELECTRODE AND INTENDED FOR A MEDICAL RADIATION APPARATUS

(75) Inventors: Wilhelmus Johannes Petrus Habraken, Eindhoven; Cornelis Henricus Martinus Van Horne, Weert; Casparus Willibrordus Kruijer, Eindhoven, all of (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/741,925

(22) Filed: Dec. 20, 2000

(30) Foreign Application Priority Data

Dec. 24, 1999 (EP) .............................................. 99204549

(51) Int. Cl.[7] ........................... H05G 1/54; G01R 27/00
(52) U.S. Cl. ........................ 378/117; 378/95; 378/197; 378/205; 324/690; 324/756
(58) Field of Search ........................... 378/117, 95, 205, 378/197, 195, 196; 324/601, 690, 756 757, 758

(56) References Cited

U.S. PATENT DOCUMENTS

| | | | | |
|---|---|---|---|---|
| 4,969,170 A | * | 11/1990 | Kikuchi et al. ............... | 378/95 |
| 4,987,583 A | * | 1/1991 | Travanty et al. .............. | 378/95 |
| 5,583,443 A | * | 12/1996 | McMurtry et al. .......... | 324/690 |
| 5,651,044 A | | 7/1997 | Klotz, Jr. .................... | 378/117 |
| 5,654,997 A | * | 8/1997 | Brownell et al. ........... | 378/117 |
| 5,828,221 A | * | 10/1998 | Habraken et al. ........... | 324/601 |
| 5,883,935 A | * | 3/1999 | Habraken et al. ........... | 378/117 |

\* cited by examiner

*Primary Examiner*—Drew Dunn
(74) *Attorney, Agent, or Firm*—John Vodopia

(57) ABSTRACT

An apparatus for medical diagnosis and/or therapy is provided with an electromagnetic object sensor in order to prevent collisions between movable parts and, for example, a patient to be examined. The sensor may be provided with sensor electrodes 16 and 18 for capacitive detection of obstacles. In order to extend the area of sensitivity of the sensor electrodes in such a manner that it encloses the area in front of the X-ray entrance window 20 of the image intensifier 6, an additional electrode is provided in the beam path between the X-ray source 4 and the image intensifier, which additional electrode is coupled to sensor electrodes 18. The additional electrode includes a carrier which is provided with a thin metal layer, both being transparent to X-rays. The additional electrode may be subdivided into sectors 28-1, . . . , 28-4 which correspond to sectors 18-1, . . . , 18-4 of the sensor electrode in such a manner that the position of an obstacle relative to the image intensifier can be determined.

6 Claims, 3 Drawing Sheets

ELECTROMAGNETIC OBJECT DETECTOR PROVIDED WITH AN ADDITIONAL ELECTRODE AND INTENDED FOR A MEDICAL RADIATION APPARATUS

BACKGROUND OF THE INVENTION

The invention relates to an apparatus for medical X-ray diagnosis and/or X-ray therapy which includes a detection device for electromagnetic detection of the presence of an object in the vicinity of a movable part of the apparatus, and also includes:

- at least one sensor electrode which is mounted on the movable part in order to produce an electromagnetic field in the vicinity of this sensor electrode,
- at least one sensor electrode which is mounted on the movable part in order to detect an electromagnetic field in the vicinity of this sensor electrode,
- a receiver for receiving, via a sensor electrode, an input signal which corresponds to the electromagnetic field in the vicinity of the sensor electrode, and
- an additional electrode.

An apparatus of this kind is known from U.S. Pat. No. 5,651,044.

An apparatus for medical diagnosis and/or therapy may be provided with a radiation transmitter and a radiation receiver. An example in this respect is formed by a medical X-ray apparatus which is provided with an X-ray source and an X-ray detector, which is usually referred to as an image intensifier. These two elements are arranged at some distance from one another and the patient to be examined or treated is positioned between the X-ray source and the image intensifier. The X-ray source and the image intensifier are positioned relative to the body of the patient in such a manner that an image can be formed of the desired cross-section of the body (the object). The orientation and the position of such apparatus can often be adjusted by means of a motor drive. Generally speaking, in the context of the present invention an object is to be understood to mean the body of a patient to be examined or another object to be examined, the body or a part of the body of a person operating the apparatus, parts of the apparatus itself (for example, the patient table) or of neighboring apparatus, or other obstacles which could invade the path of movement of the parts of the apparatus.

Many of such apparatus are provided with a so-called C-arm, that is, a circular carrier which is rotatable in its own plane (so about an axis extending perpendicularly to the plane in which the C-arm is situated) by way of a trackway, its own plane being rotatable about an axis situated in said plane. Furthermore, a number of other possibilities of displacement also exist.

During the use of the apparatus it is important that a movable part, for example the image intensifier, closely approaches the object to be examined so that the desired clarity and magnification factor of the image can be attained. The image intensifier has a comparatively large front surface for receiving the X-rays and each point on this front surface or on its circumference could come into contact with the object to be examined. Such a collision can take place in any direction of movement of the image intensifier. This is undesirable and, therefore, such an apparatus is provided with a detection device for the detection of the presence of an object in the vicinity of the movable part of the apparatus. It is important to install such a detection device notably in the case of motor-driven apparatus. When the presence of an object is detected within a given small distance from the movable part of the object, the motion of (said part of) the apparatus can be stopped so as to prevent a collision.

The cited U.S. Pat. No. 5,651,044 discloses a medical X-ray apparatus with a capacitive collision sensor which is capable of detecting the presence of an object within a given distance from the movable part (the image intensifier) of the apparatus. The apparatus is provided with a signal source for producing an electric signal which is applied to a sensor electrode mounted on the outer circumference of the image intensifier. An electromagnetic field is thus produced in the vicinity of this sensor electrode; also connected to the sensor electrode is a signal receiver which receives a signal which corresponds to the electromagnetic field in the vicinity of the sensor electrode. This signal is further processed by means of a processing unit which produces an output signal corresponding to the field strength. This known detection device utilizes the same sensor electrode for the production as well as the detection of the field strength.

The known detection device is also provided with one or more additional electrodes for the electromagnetic shielding of the sensor electrodes for the detection of the presence of other components of the X-ray apparatus, such as the image intensifier itself or the slide on which it moves.

The sensor electrodes of the known detection device are mounted around the X-ray receiving window of the image intensifier. Because the X-ray receiving window of an image intensifier may be comparatively large, particularly at the center of this (often approximately circular) window there are regions which lie outside the sensitive area of the sensor electrodes, so that in these regions the proximity of the object to be examined cannot be detected or only inadequately so.

BRIEF SUMMARY OF THE INVENTION

It is an object of the invention to provide an apparatus of the kind set forth in which the detection of the proximity of an object to be examined is enhanced.

To this end, the apparatus according to the invention is characterized in that the additional electrode is RF coupled to at least one sensor electrode, which additional electrode is arranged in the beam path between the X-ray apparatus and in the sensitive area of said sensor electrode, and which additional electrode includes a carrier of a material which is substantially transparent to X-rays, said carrier supporting a layer of an electrically conductive material of a thickness such that this layer is substantially transparent to X-rays.

The sensitive area of the detection device is expanded by the RF coupling of the additional electrode to the sensor electrode. The arrangement of the additional electrode in the beam path of the apparatus ensures that this electrode covers exactly the region in which a reduction of the intensity occurs in the known apparatus. The original region covered by the sensor electrode remains the same. Because the carrier of the additional electrode and the layer of electrically conductive material are both substantially transparent to X-rays, the additional electrode does not form an obstacle for the X-rays to be detected.

The movable part in a first embodiment of the invention is formed by an X-ray detector whose X-ray receiving side has a substantially cylindrical shape, the sensor electrodes being constructed so as to be strip-shaped and being arranged in a mutual parallel arrangement in the same plane around the cylindrical shape whereas the additional electrode is arranged directly in front of the X-ray receiving side of the X-ray detector. The strip-shaped sensor electrode, or assembly of sensor electrodes, in this embodiment creates a sensitive area which is situated mainly in the vicinity of the edge of the X-ray receiving window of the apparatus; if a plurality of sensor elements are present (for example, separate transmitter and receiver electrodes), they are arranged so as to extend parallel to one another. Because of the strip-like shape of the electrodes, a preferred orientation for the sensitivity is avoided. The additional electrode can be formed as a circular plate which is arranged directly in front of the X-ray receiving window; it should be proportioned such that the edge of this plate very closely approaches the edge of the sensor electrode.

The strip-shaped sensor electrode in a further embodiment of the invention is subdivided into a number of N parts, the additional electrode being subdivided into a corresponding number of N sectors, each of said sectors being situated opposite a respective one of said parts of the detection electrode. This step enables the detection of not only the presence of an obstacle, but also of the position of the obstacle relative to the X-ray detector, for example, by determination of the difference in the strength of the signals from the various sectors. On the basis of said information the direction can be decided in which the apparatus must displace the image intensifier so as to avoid an impending collision.

In another embodiment of the invention the RF coupling between the additional electrode and the sensor electrode is realized without a physical connection. In this embodiment the sensor electrode and the additional electrode must be arranged so near one another that a capacitive coupling is realized between the two types of electrode. Because of the absence of physical electrical connections, the advantage is achieved that no expert personnel is required so as to remove and re-install the additional electrode, for example, in the case of cleaning of the image intensifier.

The carrier in a preferred embodiment of the invention is made of a synthetic material. Because many synthetic materials consist mainly of light elements such as hydrogen and carbon, the required X-ray transparency is achieved by the choice of this carrier material.

The layer of electrically conductive material in a further embodiment consists of aluminium and/or nickel. These materials are comparatively highly transparent to X-rays and can be deposited in such thin layers that the thickness of the layer does not impose a restriction from a point of view of X-ray absorption.

BRIEF DESCRIPTION OF THE DRAWINGS

The invention will be described in detail hereinafter with reference to the Figures. Therein.

DETAILED DESCRIPTION OF THE INVENTION

Figure 1:
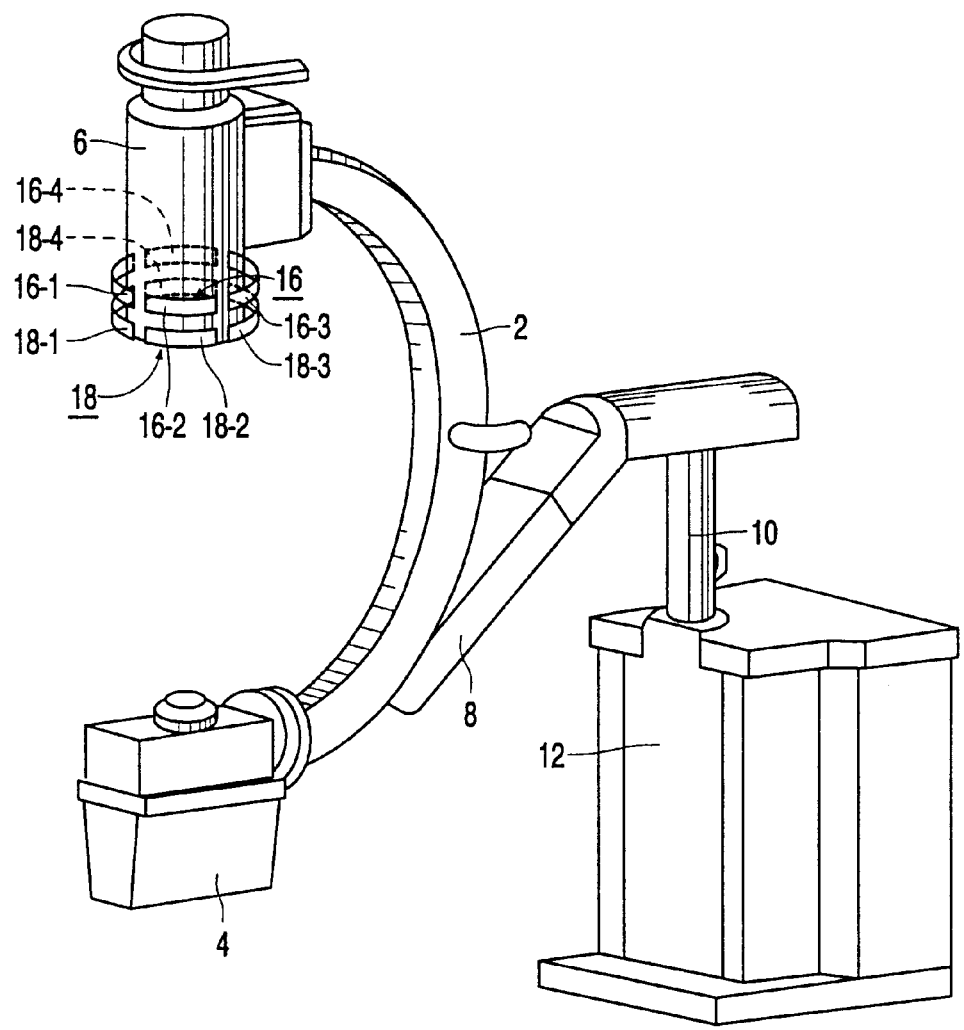
FIG. 1 is a general view of a medical X-ray apparatus in which electromagnetic detection of the presence of an obstacle can be realized.

FIG. 1 is a general view of a medical diagnostic and/or therapy apparatus in the form of an X-ray apparatus. The X-ray apparatus includes a carrier 2 on which there are mounted an X-ray source 4 and an X-ray image intensifier 6. The carrier is shaped as an arc of a circle which can be rotated, by way of a trackway 8, about an axis which extends perpendicularly to the plane of the arc of a circle. This type of carrier is known as a C-arm; generally speaking, such arms are also rotatable about an axis which is situated in the plane of the circular arc. The rotation mechanism for the latter motion is not shown in the Figure. The assembly formed by the carrier 2 and the trackway 8 is also rotatable about a shaft 10. This shaft is mounted on a stand 12 which may be constructed so as to be mobile, if desired. The X-ray source 4 and the X-ray detector 6 are preferably also displaceable relative to the carrier 2. For easy displacement of these components they are provided with a motor drive (not shown in the Figure). The object to be examined, in this case being the body of the patient to be examined or treated, is arranged on a table (not shown in the Figure) which is situated between the image intensifier 6 and the X-ray source 4. As a result of the described possibilities for motion of the C-arm 2, the image intensifier 6, and the X-ray source 4, these components can be oriented relative to the patient in all desired directions so as to form images of all desired cross-sections.

The displaceability of the image intensifier 6 relative to the carrier 2 is realized by way of the presence of a slide 14 on which the image intensifier can be moved to and fro along an imaginary connecting line between the X-ray source 4 and the image intensifier 6. Because of its mobility, a movable part, such as the image intensifier 6, can readily come into contact with the body of a patient to be examined or with other obstacles. This is undesirable and, therefore, the image intensifier in the present embodiment is provided with a detection device for the detection of the presence of an object in the vicinity of the movable part of the apparatus. The detection device includes a sensor electrode 16 which acts as a transmission electrode and a sensor electrode 18 which acts as a detection electrode. The transmission electrode 16 is formed by an annular electrode which is arranged around the end of the image intensifier 6 and serves to generate an electromagnetic field in the vicinity thereof. The detection electrode is formed by an annular electrode 18 which is arranged around the end of the image intensifier 6 and in the vicinity of the electrode 16 in order to detect the electromagnetic field which is produced by the electrode 16 and distorted by the object to be detected. In order to achieve directional sensitivity, the annular electrodes 16 and 18 may be subdivided into ring sectors 16-1, 16-2, 16-3 and 16-4 and 18-1, 18-2, 18-3 and 18-4, respectively. The procedure for applying signals to and for removing signals from said electrodes is not of essential importance to the implementation of the invention and, therefore, will not be elaborated upon herein.

Figure 2:
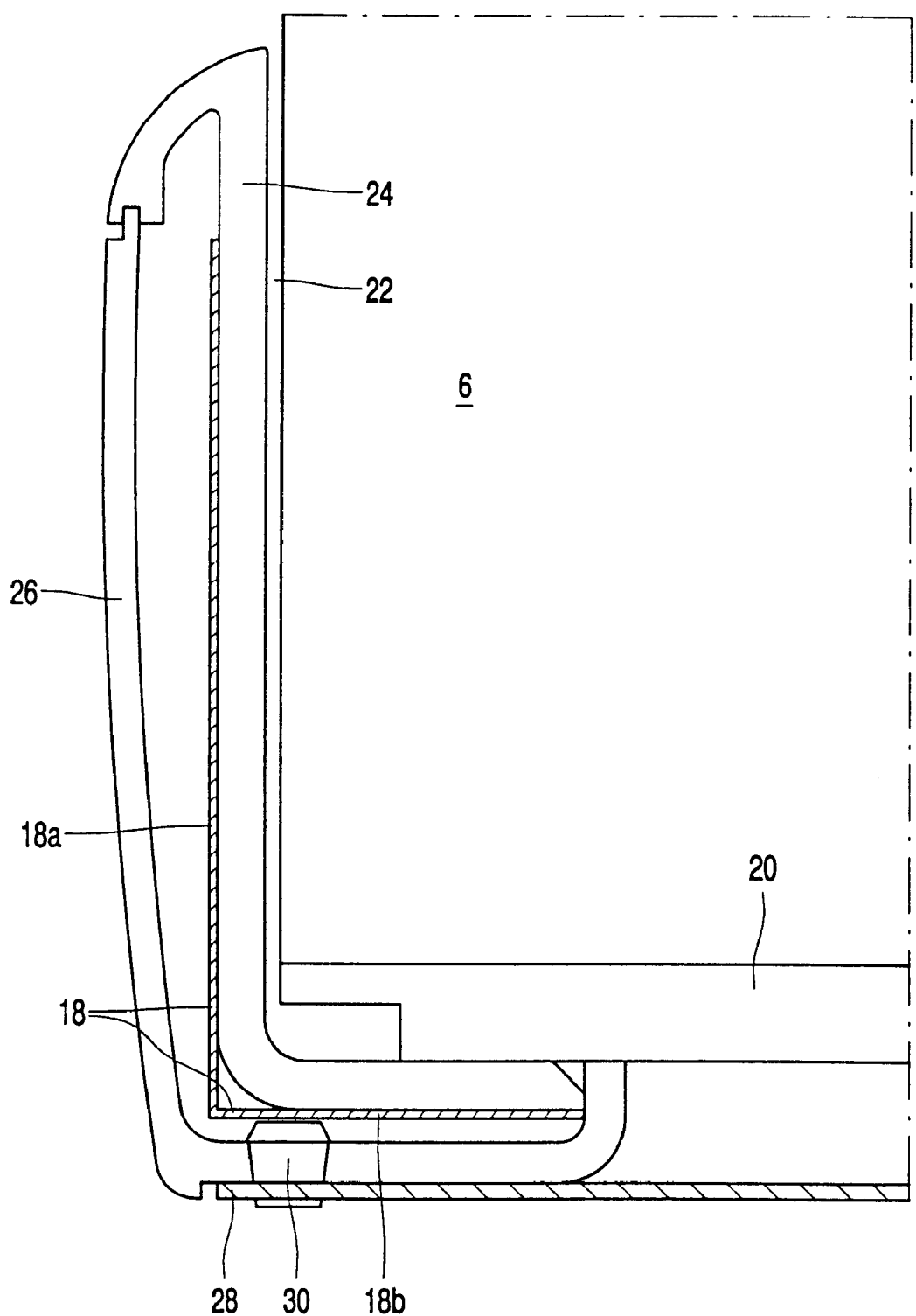
FIG. 2 is a sectional view of a detail of the electrodes according to the invention.

FIG. 2 is a sectional view of a detail of the electrodes according to the invention. It is assumed that the image intensifier 6 is shaped as a circular cylinder whose axis coincides with the connecting line between the X-ray source 4 and the image intensifier 6. FIG. 2 is a sectional view in a plane which extends through one of the sensor electrodes (for example, the electrode 18-1) and contains said axis, only one corner of the image intensifier 6 being depicted. The sensor electrode 18 consists of a strip-shaped part 18$a$ which extends transversely of the plane of drawing and is arranged around the cylindrical image intensifier 6 and of an annular part 18$b$ which is formed from a flat plate, is arranged perpendicularly thereto and is subdivided, if desired, into sectors, said part 18$b$ being arranged at the edge of the image intensifier and partly in front of the X-ray receiving window 20 of the image intensifier 6. Between the housing 22 of the image intensifier and the electrode 18 there is provided a part 24 of a cover of a synthetic material which adjoins a part 26 of the synthetic cover. Parallel to the annular part 18b of the sensor electrode 18 there is provided the additional electrode 28 which consists of an X-ray transparent carrier of a synthetic material on which there is provided a thin metal layer of aluminium or nickel, the thickness of said layer being such that it is electrically conductive but still transparent to X-rays.

The additional electrode is positioned in such a manner that it is situated in the beam path of the X-ray apparatus and in the sensitive area of the part 18b of the sensor electrode 18. The distance between the part 18b and the additional electrode 28 is chosen to be such that because of their mutual capacitance an RF coupling exists between the two electrodes. The capacitance between the two electrodes amounts to approximately 1 pF in the case of a signal frequency of the electromagnetic sensor field of 100 kHz, a distance of 5 mm between the two electrodes, and a mutually visible surface area of 20 $cm^2$.

Should said capacitance be too small so as to realize the desired RF coupling, a coupling capacitor or even a conductive connection between the two electrodes may be provided. The additional electrode 28 may be attached to the housing of the image intensifier by way of a snap connection 30 so that the additional electrode can be used in a simple manner and without using special tools, for example for technical maintenance for the cleaning of the various parts.

Figure 3:
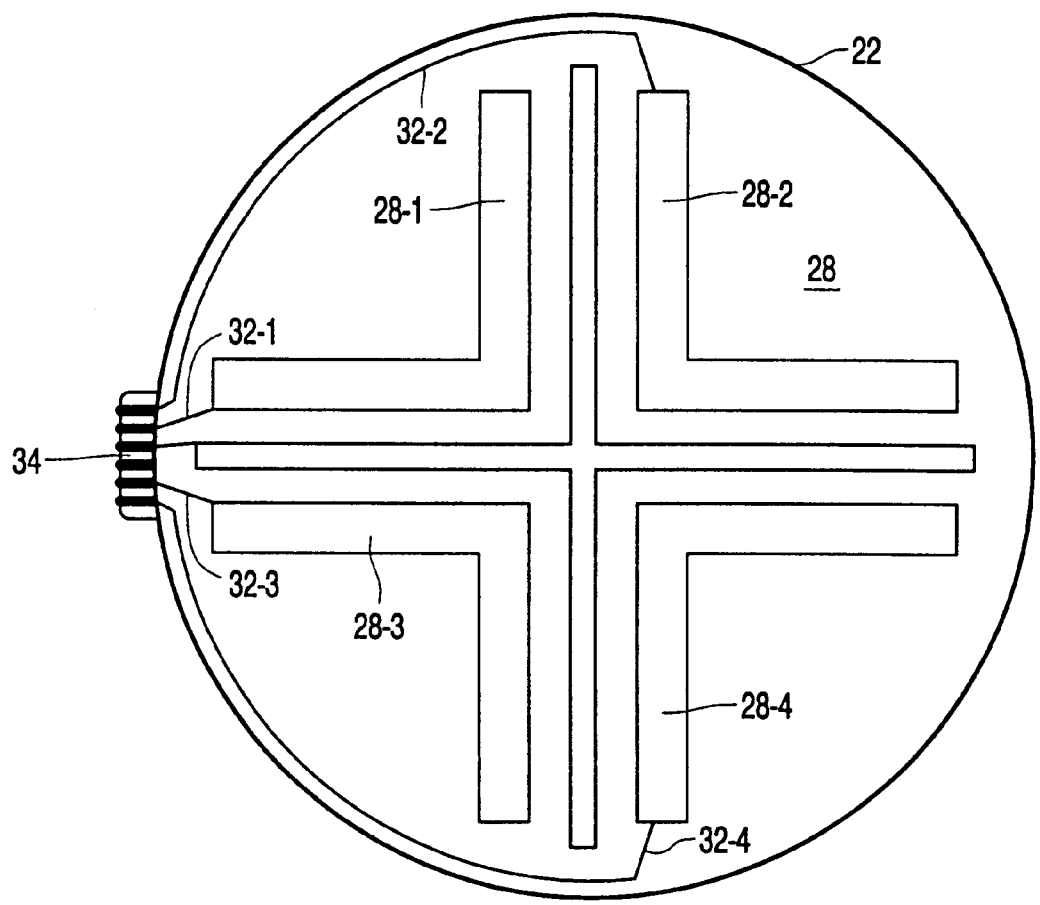
FIG. 3 is a front view of an electrode configuration of the additional electrode according to the invention.

FIG. 3 is a front view of an electrode configuration of the additional electrode according to the invention. This Figure is a front view of the X-ray receiving window which, therefore, is situated in the plane of drawing in this Figure so that the housing 22 of the image intensifier is visible as a circle in the Figure. The additional electrode 28 is arranged in front of the X-ray receiving window 20, so that it is situated above the plane of drawing. In the electrode configuration shown herein the additional electrode 28 is subdivided into four equal sectors 28-1 to 28-4, each of which corresponds to a part of the sensor electrode 18 which is also subdivided in a sector-like manner, notably the part 18b thereof which is not shown in FIG. 3. In this embodiment the sectors 28-1 to 28-4 are conductively connected, via connections 32-1 to 32-4 and a connector 34, to the other parts of the detection device.

It is to be noted that the sensitive area of the sensor electrodes can be increased by means of an additional electrode which extends only across a part of the X-ray receiving window. It is merely important that this electrode is situated in an area that, according to the state of the art, was not available for the mounting of electrodes, that is, the beam path between the X-ray source and the image intensifier of the X-ray apparatus.

What is claimed is:
1. An apparatus for medical X-ray diagnosis and/or X-ray therapy which includes a detection device for electromagnetic detection of the presence of an object in the vicinity of a movable part (6) of the apparatus, and also includes:
   at least one sensor electrode (16) which is mounted on the movable part (6) in order to produce an electromagnetic field in the vicinity of this sensor electrode,
   at least one sensor electrode (18) which is mounted on the movable part in order to detect an electromagnetic field in the vicinity of this sensor electrode,
   a receiver for receiving, via a sensor electrode, an input signal which corresponds to the electromagnetic field in the vicinity of the sensor electrode, and
   an additional electrode (28), characterized in that
   the additional electrode (28) is RF coupled to at least one sensor electrode (18),
   which additional electrode is arranged in the beam path of the X-ray apparatus and in the sensitive area of said sensor electrode (18), and
   which additional electrode includes a carrier of a material which is substantially transparent to X-rays, said carrier supporting a layer of an electrically conductive material of a thickness such that this layer is substantially transparent to X-rays.
2. An apparatus as claimed in claim 1, wherein
   the movable part is formed by an X-ray detector whose X-ray receiving side has a substantially cylindrical shape,
   the sensor electrodes (18) are constructed so as to be strip-shaped and are arranged in a mutual parallel arrangement in the same plane around the cylindrical shape, whereas
   the additional electrode (28) is arranged directly in front of the X-ray receiving window (20) of the X-ray detector.
3. An apparatus as claimed in claim 2, wherein the strip-shaped sensor electrode (18) is subdivided into a number of N parts (18-1, . . . , 18-4) and the additional electrode (28) is subdivided into a corresponding number of N sectors (28-1, . . . , 28-4), each of said sectors being situated opposite a respective one of said parts of the detection electrode.
4. An apparatus as claimed in claim 1, wherein the RF coupling between the additional electrode and the sensor electrode is realized without a physical connection.
5. An apparatus as claimed in claim 1, wherein the carrier is made of a synthetic material.
6. An apparatus as claimed in claim 1, wherein the layer of electrically conductive material consists of aluminium and/or nickel.

* * * * *